United States Patent

Björk et al.

[11] Patent Number: 5,804,217
[45] Date of Patent: Sep. 8, 1998

[54] MANUFACTURING MATRICES

[75] Inventors: Seth Björk, Hägersten; Ragnar Ek, Stockholm; Gert Ragnarsson, Bro, all of Sweden

[73] Assignee: Pharmacia & Upjohn Aktiebolag, Stockholm, Sweden

[21] Appl. No.: 532,716

[22] PCT Filed: Apr. 14, 1994

[86] PCT No.: PCT/SE94/00331

§ 371 Date: Oct. 11, 1995

§ 102(e) Date: Oct. 11, 1995

[87] PCT Pub. No.: WO94/23703

PCT Pub. Date: Oct. 27, 1994

[30] Foreign Application Priority Data

Apr. 14, 1993 [SE] Sweden ................................. 9301220

[51] Int. Cl.⁶ ................................................... A61K 9/20
[52] U.S. Cl. .......................... 424/488; 424/464; 424/468; 427/2.14
[58] Field of Search ..................... 424/468, 464, 424/488, 495, 494, 498, 490, 497; 427/2.14; 264/15, 6, 7, 41, 109, 413, 417

[56] References Cited

U.S. PATENT DOCUMENTS

| | | | |
|---|---|---|---|
| Re. 35,460 | 2/1997 | Klungness et al. | 162/9 |
| 3,297,806 | 1/1967 | Battista et al. | 264/129 |
| 3,873,694 | 3/1975 | Kanig | 424/648 |
| 4,055,510 | 10/1977 | Peska et al. | 536/57 |
| 4,090,022 | 5/1978 | Tsao et al. | 435/179 |
| 4,138,475 | 2/1979 | McAinsh et al. | 424/19 |
| 4,269,859 | 5/1981 | Morse | 424/362 |
| 4,464,224 | 8/1984 | Matolesy | 162/111 |
| 4,572,833 | 2/1986 | Pedersen et al. | 424/467 |
| 4,606,909 | 8/1986 | Bechgaard et al. | 424/469 |
| 4,775,535 | 10/1988 | Lowey | 424/468 |
| 4,806,360 | 2/1989 | Leong et al. | 424/487 |
| 4,808,413 | 2/1989 | Joshi et al. | 424/458 |
| 4,855,143 | 8/1989 | Lowey | 424/468 |
| 4,900,558 | 2/1990 | Barry et al. | 424/461 |
| 5,049,394 | 9/1991 | Howard et al. | 424/490 |
| 5,223,090 | 6/1993 | Klungness et al. | 162/9 |
| 5,292,461 | 3/1994 | Juch et al. | 264/37 |
| 5,302,396 | 4/1994 | Phadke et al. | 424/465 |
| 5,508,044 | 4/1996 | Buxton et al. | 424/495 |
| 5,601,845 | 2/1997 | Buxton | 424/495 |
| 5,607,695 | 3/1997 | Ek et al. | 424/468 |

FOREIGN PATENT DOCUMENTS

| | | |
|---|---|---|
| 0 270 305 A2 | 6/1988 | European Pat. Off. . |
| 0 270 305 A3 | 6/1988 | European Pat. Off. . |
| 0 303 259 A2 | 2/1989 | European Pat. Off. . |
| 0 303 259 A3 | 2/1989 | European Pat. Off. . |
| 0 466 986 A1 | 1/1992 | European Pat. Off. . |
| 1575700 | 9/1980 | United Kingdom . |
| 91/18590 | 12/1991 | WIPO . |
| WO 91/18590 | 12/1991 | WIPO . |

OTHER PUBLICATIONS

Yamauchi et al., Development of the Pore Structure of Paper Web during Consolidation, J. Japan Wood Res. Soc., Mokuzai Gakkaishi, vol. 25, No. 6, (1979), pp. 414–421.

British Pharmacopoeia, vol. 1, 1993, Cellulose, pp. 119–120.

English Abstract of Japanese 89–1272643 (Oct. 1989).

Bogentoft et al., Influence of Food on the Absorption of Acetylsalicylic Acid from Enteric–Coated Dosage Forms, Europ. J. Clin. Pharmacol. 24, 351–355 (1978), pp. 351–355.

Ragnarsson et al., Coated Drug Cores in Multiple Unit Preparations Influence of Particle Size, Drug Development and Industrial Pharmacy, 14(15–17), pp. 2285–2297 (1988).

Battista, Hydrolysis abnd Crystallization of Cellulose, Industrial and Engineering Chemistry, vol. 42(3), pp. 502–507. 1950.

Nystrom et al., Measurement of axial and radial tensile strength of tablets and their relation to capping, Acta Pharm. Suec. 15, pp. 226–232 (1978).

*Primary Examiner*—S. Mark Clardy
*Assistant Examiner*—Robert H. Harrison
*Attorney, Agent, or Firm*—Pollock, Vande Sande & Priddy

[57] ABSTRACT

Porous cellulose matrices with a defined particle size and a significantly higher porosity (i.e. pore volume) than conventional formulations, such as pellet formulations containing cellulose and binders are prepared. The cellulose is mechanically treated with low adhesion to the process equipment during a controlled gradual addition of an aqueous based fluid, optionally containing a surface-active ingredient, into regular particles, which are finally dried to obtain dry porous cellulose matrices. The so obtained matrices can be used as carriers for bioactive substances in multiple-unit preparations or tablets.

30 Claims, No Drawings

MANUFACTURING MATRICES

This application has been filed under 35 USC 371 as the national stage of international application PCT/SE94/00331, filed Apr. 14, 1994.

FIELD OF INVENTION

The present invention relates to a manufacturing process for multiple unit carriers and release controlling systems for bioactive substances from a wide variety of cellulose raw materials. It is also directed to the manufacture of additives to be used in tablet formation, especially in direct compression and to obtain multiple unit preparations in the form compressed and disintegrating tablets.

BACKGROUND OF THE INVENTION

The background of the present invention is previously disclosed in the international patent application WO 91/18590, published 12 Dec. 1991, which application also is referred to for a prior art review.

WO 91/18590 discloses a process for the manufacture of porous cellulose matrice particles, which have regular shape, and a capacity of sorbing 1.5–9 times of their own weight of water, a tap bulk density of less than 0.85 g/ml. The process for the manufacture of these porous cellulose matrices were performed by a mechanical treatment of hydrolyzed cellulose in a wet stage. The cellulose matrices preferably have a size of at least 0.1 mm and a tap bulk density of 0.1–0.7 g/ml.

According to this patent specification the bioactive substance or bioactive substances can be sorbed, precipitated or sublimized into the porous structure of the matrices. The matrices can also be admixed with bioactive substances or granules containing bioactive substances in order to improve the tabletting and tablet properties and thereafter compressed.

The manufacturing process according to this earlier patent application was found to give excellent results for wet hydrolyzed cellulose raw materials with suitable plastic properties. It was found possible to obtain reproducible properties of the porous matrices by controlling the hydrolysis and the mechanical treatment process. Commercial qualities of microcrystalline cellulose such as Avicel (FMC Corp), Emocel (Finn Sugar, Finland) and Dynacel (Cellupharm AB, Sweden) were found to give more dense particles, less suitable in many applications. Furthermore, it was found that the use of established microcrystalline cellulose qualities led to unacceptable differences in form, size and size distribution.

However, this manufacturing previously disclosed process is limited to wet celluloses subjected to chemical hydrolyzation, which is a disadvantageous restriction in the choice of raw materials. The use of wet hydrolysed cellulose is also connected with problems related to bacterial growth, especially in cases when the cellulose is not subjected to immediate processing. Furthermore, the hydrolysis process can be difficult to stop before it has reached the levelling off degree of polymerisation, at which stage the processed batch essentially contains microcrystalline cellulose. The process according to WO 91/18590 is preferably performed by a mechanical treatment followed by a forming step in a cyclone. Such a process is satisfying in a large-scale industrial context, but it will be less suitable for a production in a smaller scale. Therefore a demand exists for a process for preparation of the porous cellulose matrices in a smaller and more convenient units like high shear mixers.

In the former process disclosed in WO 91/18590 there is no method adviced for drying the cellulose particles. The drying shrinkage has been noticed as a problem when loading the matrice particles with an agent dissolved in a liquid, which does not re-expand the particles by swelling.

A problem related to the drying shrinkage is that a film coating on the matrice particle may burst when the particle re-expands in contact with an aqueous fluid.

It is the object of the present invention to provide a process which overcomes the above mentioned problems as well as satisfying the demand of being applicable on a wide variety of raw materials.

DESCRIPTION OF THE INVENTION

The present invention is directed to the process for the manufacture of porous cellulose matrices with a defined particle size and a significantly higher porosity (i.e. pore volume) than conventional formulations, such as pellet formulations containing cellulose and binders. The process is applicable on a wide variety of substantially dry and preferably pure cellulose raw materials, e.g. as disclosed in British Pharmacopoeia 1993, vol. 1, Effective date: 1 Dec. 1993, London: HMSO, p. 119–120. The cellulose is mechanically treated with low adhesion to the process equipment during a controlled gradual addition of an aqueous-based fluid, optionally containing a surface-active ingredient, into regular particles, which are finally dried to obtain dry porous cellulose matrices.

The so obtained matrices can be loaded with one or several bioactive substance or substances and can optionally be incorporated in a suitable carrier, such as a gelatine capsule to form a multiple-unit preparation, or they can be compressed into tablets, if suitable by the addition of tabletting excipients.

The manufacturing process is based on a simple mechanical treatment of the cellulose raw material which is added to a mixing step in a dry or substantially dry state. The mechanical treatment is performed in a low-adhesion high shear mixer with a controlled, gradual supply of an aqueous-based fluid. Low adhesion mixers are constructed with a very smooth surface or a surface covered with materials such as PTFE (Teflon®, Du Pont, USA), in order to reduce the adhesion, which increases the yield of acceptable cellulose particles according to the invention.

An especially preferred type of mixer is a low-adhesion high shear mixer with a spraying device, such as an atomizer, for the supply of the aqueous-based fluid. A suitable type of mixer is the Pellmixer from Niro A/S, Denmark.

It is possible to precede the said treatment step with a pre-mixing step of cellulose and an aqueous fluid. The pre-mixing can be performed in conventional mixing devices, such as a planetary mixer. The mixed batch is thereafter charged into the low adhesion mixing device for completing the mechanical treatment.

After completing the mechanical treatment the batch of produced cellulose matrices will pass a drying procedure. The drying can be performed with standard equipment, for example on trays in an oven at a moderately elevated temperature, by a rotary evaporator, in fluidized beds, and by means of microwaves. The pressure during the drying processes can be atmospheric or reduced.

A suitable drying procedure according to the invention is freeze-drying. It is notable that the matrices, which are freeze-dried, do not shrink to the same extent as matrices subjected to other drying procedures. A freeze-drying procedure also increases the matrice porosity and maintains the roundness of the matrice particles. The general teachings of freeze-drying of cellulose webs for increasing the porosity disclosed in J. Japan Wood Res. Soc. Vol. 25, No. 6, 1979, p. 414–21 ( T. Yamauchi et. al.) are applicable on the inventive matrices.

The aqueous-based fluid supplied during the manufacturing process is added in a total amount 80–500% of the dry weight of the cellulose material and can be mixed with another solvent such as ethanol.

An addition of an alcohol, such as ethanol, in the process fluid will also increase the matrice porosity by decreasing the contracting surface tension forces and by limiting or completely avoiding hydration of the cellulose fibres. An addition of a surface-active agent in the aqueous-based fluid can also reduce the shrinking of the matrices during the drying procedure due to a reduced surface tension in the aqueous medium.

Suitable surface-active agents are polyoxyethylene sorbitan fatty acid esters (Tweens), but anyone skilled in the technique will have no problems to find alternative agents.

It must be emphasised that there are applications where the aforedescribed re-expanding by swelling in water contact phenomenon is advantageous. For example a delivery of an initial release of a bioactive substance to an aqueous medium can be accomplished if a certain fraction of multiple unit are designed to burst in water contact. Another way of using the swelling properties of the matrices is to include a certain fraction of highly swelling matrices in a population of matrices which are compressed to a tablet in order to disintegrate it in a controlled manner in the gastrointestinal tract. It will be within the scope of the present invention to use controlled swelling of the matrices as a controlled release device for bioactive substances from cellulose matrices, to include a certain amount of such bursting particles in a population of multiple units and to use such matrices as disintegrating means in a tablet.

The variation of process parameters, such as impeller speed, the supply rate and the composition of the aqueous mixing fluid will have influence on the product quality of the porous cellulose matrices. Any such parameter variations will, however, be easy for a person skilled in the art to identify and to utilize the advantages thereof, and it is to be considered that any such modifications of the process is covered by the appended patent claims.

It is notable that the inventive process can produce the cellulose matrices with the desired properties from a wide variety of dry cellulose raw materials, preferably of other sources than chemically hydrolyzed celluloses. Suitably, the cellulose raw material is substantially pure, preferably of a pharmaceutical purity grade. It is also conceivable to use one or more derivatives of cellulose as raw materials, such as carboxy methylcellulose (CMC), optionally in any mixture with cellulose.

A suitable type of cellulose raw material is SOLKA-FLOC™ (Mendell, USA), but also the dry fibrous materials disclosed in the patent specification U.S. Pat. No. 4,464,224, column 4, lines 4–10 are considered as suitable alternatives. When choosing suitable raw materials for the inventive process it is important that the mean fibre length of the cellulose is less than the desired mean diameter of the resulting porous particles.

It will generally be no problem to find suitable raw materials among dry and preferably pure celluloses for a person skilled in the art.

It is also an important condition in the process according to the present invention that the cellulose raw materal initially is substantially dry, having at least 70% solids, suitably at least 80% and preferably at least 90% solids (see also patent specification U.S. Pat. No. 4,464,224, column 4, lines 10–35). Subsequently, the substantially dry cellulose raw material is wetted by a gradual supply of an aqueous-based liquid during the manufacturing to porous matrices.

It is furthermore an important condition that the cellulose raw material is initially pure, when the process according to the invention is used to produce cellulose matrices for pharmaceutical use. Celluloses fulfilling this criteria are those that are sufficiently pure, optionally after washing with a washing agent, so that the cellulose matrices produced according to the present invention meet the standard for powdered cellulose set by e.g. the British Pharmacopoeia 1993, p. 120. Thus, in the present invention the content of ether-soluble substances should be below 0.15% (w/w) and/or the content of water-soluble substances should be below 1.0% (w/w).

Prior to optional loading of bioactive substances, the porous cellulose matrices used to prepare the multiple unit preparations and tablets according to the present invention, suitably contain less than 0.15% (w/w) of ether-soluble substances and less than 1.0% (w/w) of water-soluble substances according to the test method for powdered cellulose in British Pharmacopoeia 1993, vol. 1, Effective date: 1 Dec. 1993, London: HMSO, p. 120.

The mainly spherical porous cellulose matrices manufactured according to the process of the present invention have a reproducible porosity, particle size i.e. largest diameter, and size distribution in the particle range of about 0.1 to 3 mm, preferably between 0.3 and 2 mm, and have a tap bulk density lower than 0.8 g/ml, preferably less than 0.7 g/ml.

These cellulose matrices are especially useful in the manufacture of multiple unit preparations (MU preparations) containing bioactive substances, which are incorporated in the matrices in a second step.

The release of the bioactive substances from the matrices can be controlled by adjusting the porosity (the porous diffusion retarding network inside the matrices) during the manufacturing process, by selecting suitable cellulose fibres, by including release modifying substances into the matrices or by applying a barrier coating (release modifying membrane). It is possible to use soluble additives, such as sodium chloride in solid form included together with the cellulose before the mechanical treatment and thereafter dissolved from the matrices in order to further increase the porosity. In certain applications water insoluble substances can be added as porosity increasing additives which thereafter are dissolved in an organic solvent, see e.g. the Japanese Patent Specification 1272643.

One or several bioactive substances and/or agents for modifying the stability, release rate or bioavailability of the bioactive substances can be applied, in any mixture or sequence, to the porous structure of the cellulose matrices in a solid, liquid, semi-liquid or gaseous form. The applied bioactive substances and/or agents are preferably a solid, a solution, a suspension, an emulsion, an oil, a super-critical fluid, a gas or a melt which can be sorbed, precipitated or sublimized into the porous structure in one or several steps, optionally with intermediate drying. If the one or several bioactive substances and/or agents are in solid, preferably in a powdery form, a mechanical mixing step will be necessary for applying the substance or substances to the matrices surfaces and optionally into the porous network of the matrices. Such a process can lead to a variety of preparations where adsorbing forces are used for a controlled loading and/or release of substances from a matrice according to the invention.

The solid, liquid, semi-liquid or gaseous substance applied to the porous matrices can contain one or several agents or materials in order to modify the release rate of the bioactive substance. The materials for modifying the release rate are preferably selected from the group consisting of cellulose derivatives, acrylic acid derivatives, phospholipids, hydrocarbons, carboxylic acids, ethers, esters, alcohols, waxes and lipids, and mixtures thereof. The release rate can also be modified by agents such as surface-active substances to improve the dissolution rate of sparingly soluble substances and promote solubilization.

The release rate of the bioactive substance or bioactive substances can be modified by applying a release controlling coating on the surface of the spherical particles. If used, the coating is selected from the group consisting of cellulose derivatives such as ethyl cellulose, acrylic acid derivatives and copolymers thereof, hydrocarbons, carboxylic acids, esters, ethers, alcohols, waxes and lipids, and mixtures thereof.

The cellulose matrices can also be used as tabletting additives with or without incorporation of bioactive substances, especially in the form of compressed tablets and in direct compression, to obtain tablets that will disintegrate into discrete particles in water.

Tablets could be prepared by admixing the matrices prior to compaction with bioactive substances and/or granules containing bioactive substances, in order to improve the tabletting process and/or tablet properties. Tablets could be prepared also by admixing the matrices, prior to compaction, with units containing bioactive substances of similar size, such as pellets, granules or crystals, which have been coated to modify the release properties of the bioactive substances, mask unpleasant taste or to improve the stability and thereafter compressing the mixture to tablets.

When the porous cellulose matrices obtained by the process according to the invention is used for preparation of tablets the matrices loaded with bioactive substances can be directly compressed into tablets.

When using the invention in the preparation of MU formulations, the basic concept is that the porous matrices of cellulose are formed in a separate process whereafter the pharmaceutical or pharmaceuticals (or other bioactive substances) are incorporated into the matrices in a second step.

The size and size distribution of the final beads are determined in the first manufacturing step while amount of bioactive substance to be incorporated is controlled in the second step. The invention makes it possible to vary the amount of bioactive substance that can be incorporated but also to control the release rate of the bioactive substance as the cellulose network acts as a porous diffusion retarding system. The release properties may also be modified by adding suitable substances, such as polymers and waxes, during or after the incorporation of the bioactive substance or finally as a film coat.

The invention is applicable in the production and use of various bioactive substances, such as pharmaceuticals, herbicides, insecticides, fertilizers and diagnostics whenever a controlled dosing and/or release is desirable. The bioactive substance is preferably a pharmaceutical compound.

It is surprising that the simplified process according to the present invention leads to a result in the form of high quality porous cellulose particles with a high shape regularity and excellent loading properties. The process is especially advantageous compared to the previously disclosed process of WO 91/18590 by the possibility to use a wider variety of raw materials and by a more convenient treatment procedure with less preparation steps. It is also favourable in terms of its smaller and more convenient process equipment and because of the possibility to control the degree of shrinkage and swelling of the matrices.

The following examples are intended to illustrate the invention without limiting the scope of protection as comprehended from the appended claims.

EXAMPLE 1

200 g powdered cellulose (SOLKA-FLOC™ BW20, Mendell, USA) was charged into a low-friction high shear mixer with atomizer (Pellmix 1/8, Niro A/S, Denmark). 300 g water was added (18 ml/minute) via the atomizer. The impeller speed during the process was 600 revolutions per minute (RPM).

Cellulose stucked on the wall and lid of the mixer was removed and combined with the bulk after 7 minutes.

The lid was opened after adding the water, and the impeller was running at 600 RPM for 10 minutes. The product-temperature was +37° C.

The moist porous cellulose matrices were dried on a tray in an oven (+60° C., 24 hours).

Yield (0.315–1.6 mm): 182 g (91%)

Tap bulk density (0.71–1.00 mm, 1000 taps): 0.4 g/ml

EXAMPLE 2

203 g powdered cellulose (SOLKA-FLOC™ BW20, Mendell, USA) was mixed with 20 g water in a planetary mixer (Kenwood Major) for 2 minutes and thereafter charged into a low adhesion high shear mixer with atomizer (Pellmix 1/8, Niro A/S, Denmark). 284 g water was added (18 ml/minute) via the atomizer. The impeller speed during the process was 600 revolutions per minute (RPM).

Cellulose which stuck on the wall and lid of the mixer was removed and combined with the bulk after 8 minutes.

The lid was opened after adding the water, and the impeller was running at 600 RPM for 10 minutes.

The moist porous cellulose matrices were dried on a tray in an oven (+60° C., 24 hours).

Yield (0.31–51.6 mm): 139 g (71%)

EXAMPLE 3

204 g powdered cellulose (SOLKA-FLOC™, Mendell, USA) was charged into a low adhesion high shear mixer with atomizer ( 1/8, Niro A/S, Denmark). 275 g water and 27 g ethanol (95%) was added (18 ml/minute) via the atomizer. The impeller speed during the process was 600 revolutions per minute (RPM).

Cellulose stucked on the wall and lid of the mixer was removed and combined with the bulk after 9 minutes.

The lid was opened after adding the water/ethanol mixture, and the impeller was running at 600 RPM for 10 minutes. The product temperature was +37° C.

The moist porous cellulose matrices were dried on a tray in an oven (+60° C., 24 hours).

Yield (0.315–1.6 mm): 137 g (70%)

EXAMPLE 4

Tap bulk density for porous cellulose matrices (PCM) 0.71–1.00 mm 1000 taps for different cellulose qualities.

| Quality | g/ml |
| --- | --- |
| Elcema P050 | 0.42 |
| Sanacel 90 | 0.40 |
| Solka Floc BW20 | 0.42 |

Tap bulk density raw material 500 taps.

| Quality | g/ml |
| --- | --- |
| Elcema P050 | 0.45 |
| Sanacel 90 | 0.29 |
| Solka Floc BW20 | 0.26 |

This experiment shows that by processing the cellulose according to the invention the tap bulk density will be less than 0.7 g/ml.

EXAMPLE 5

Tabletting of porous cellulose matrices (PCM) prepared in accordance with the invention.

The tablets were compressed at 100 MPa using 11.3 mm flat circular punches.

PCM from the 0.71–1.00 mm fractions were used.

Mean values from 5 tablets.

| Raw material | Height (cm) | Strength (N) | Weight (mg) |
| --- | --- | --- | --- |
| Solka-Floc BW20 | 0.45 | 31 | 503 |
| Sanacel 90 | 0.43 | 105 | 500 |
| Elcema P050 | 0.45 | 48 | 502 |
| Sanacel 300 | 0.46 | 101 | 505 |

As reference:

| | | | |
| --- | --- | --- | --- |
| Avicel PH101 Granulated in water/ethanol | 0.41 | 283 | 501 |

This experiment shows that matrices according to the present invention are possible to compress to tablets.

EXAMPLE 6

Loading the Matrices with Lidocaine 1.04 g empty matrices 0.5–0.71mm according to Example 1 were charged into a 100 ml glass vessel. 77 mg lidocaine were charged into a 25 ml glass beaker and dissolved in ethanol (95%).

The solution was transferred to the vessel containing the matrices. The beaker was washed with ethanol. The ethanol was evaporated in a rotary evaporator (bath temperature approx. +45° C.) for approx. 20 minutes. Some deposits were found on the wall of the glass vessel.

The loaded matrices were transferred to a glass bottle. The net weight was 1.08g.

Release of Lidocaine 0.415 g of the loaded matrices were stirred in 360 ml 0.1M HCl at 25° C. with 150 revolutions per minute.

Samples were taken after 5, 10, 15 and 60 minutes. They were analyzed spectrophotometrically at 230 nm. All samples contained approximately 59 µg lidocaine per ml. This corresponds to 51.2 mg lidocaine per g loaded matrices. The experiment shows that matrices according to the present invention exhibit satisfying release properties of the loaded pharmaceutical.

EXAMPLE 7

Three different batches were made in a Pellmix 1/8 to investigate the pore volume in accordance with Examples 1 to 3. Two formulations with microcrystalline cellulose (Avicel 100 and 101 and binders were compared to a formulation with dry powdered cellulose (SolkaFloc BW) without binder.

| Batch A: | |
| --- | --- |
| Avicel 100 | 200 g |
| Lactose | 200 g |
| HPMC E5 | 10 g |
| Water | 270 g |
| Batch B: | |
| Avicel 101 | 500 g |
| Plasdone | 10 g |
| Water | 750 g |
| Batch C: | |
| SolkaFloc BW20 | 203 g |
| Water | 304 g |

Mercury porosimetry was used to calculate the pore volume with the following results:

| Batch A | 0.275 cm$^3$/ml |
| --- | --- |
| Batch B | 0.173 cm$^3$/ml |
| Batch C | 0.888 cm$^3$/ml |

The experiment shows that a high level of porosity is obtained when a powdered dry cellulose is processed with the inventive method and that a higher porosity is obtained when using the dry pure untreated cellulose compared to conventional pellets of highly hydrolyzed microcrystalline celluloses and binders.

EXAMPLE 8

Porous cellulose matrices in the size range of 0.71–1 mm were prepared according to Example 2 above. To 10 g of the matrices 15 g of distilled water were added. The resultant mixture rested during 24 hours before freeze-drying by sublimation of water at −20° C. It was found that the bulk density increased from 2.17 ml/g before freeze-drying to 2.48 ml/g after freeze-drying. This is a measure of an increased porosity.

The experiment shows that freeze-drying of the porous cellulose matrices as prepared according to the invention increases the porosity.

We claim:

1. A process for the manufacture of porous cellulose matrices from a cellulose raw material selected from the group consisting of cellulose, cellulose chemical derivative and mixture thereof, having a mean fiber length less than the desired mean diameter of the resulting particles and further having a solids content of at least 70%, by mechanically treating said cellulose raw material with a low-adhesion mixing device during a controlled, gradual addition of an aqueous mixing fluid, into mainly spherical particles, and finally drying the resulting particles to obtain dry porous cellulose matrices with a particle size distribution in the range of about 0.1 to 3 mm with reference to the largest diameter of the particles, and a tap bulk density less than 0.8 mg/ml in the dry state.

2. A process according to claim 1, characterized by that the low-adhesion mixing device is a low-adhesion high shear mixer to which the aqueous mixing fluid is introduced with a spraying device.

3. A process according to claim 1 characterized by that the aqueous-based fluid contains water and a surface-active agent.

4. A process according to claim 1 characterized by that the aqueous-based fluid further comprises solvent.

5. A process according to any previous claim characterized by that one or several bioactive substances, in optional mixture or sequence with agents influencing the stability, release rate and/or bioavailability of said bioactive substances, in a solid, liquid, semi-liquid or gaseous form, are sorbed, precipitated or sublimized into the porous structure of the matrices in one or several steps, optionally with intermediate drying.

6. A process according to claim 5 characterized by that the bioactive substance is a solid, solution, suspension, emulsion, oil, super-critical fluid, gas or melt.

7. A process according to claim 1 characterized by that the final drying step is selected from the group consisting of freeze-drying procedures, fluidized beds, rotary evaporation, drying by microwaves and drying the matrices conventionally on trays.

8. A process according to claim 5 characterized by that the porosity of the cellulose matrices is adjusted to control the release of the bioactive substance.

9. A process according to claim 5 characterized by that the composition of solid, liquid, semi-liquid or gaseous form, contain one or more agents or materials in order to modify the release rate or the bioavailability of the bioactive substance.

10. A process according to claim 5 characterized by that the bioactive substance or substances are supplied as powder together with cellulose matrices to a mechanical mixing step in order to apply such substance or substances to the surfaces and optionally into the porous networks of the said matrices.

11. A process according to claim 9 characterized by that the material is selected from the group consisting of cellulose derivatives, acrylic acid derivatives, phospholipids, hydrocarbons, carboxylic acids, esters, ethers, alcohols, waxes and lipids, and mixtures thereof.

12. A process according to claim 11 characterized by that the release controlling coating is selected from the group consisting of cellulose derivatives such as ethyl cellulose, acrylic acid derivatives and copolymers thereof, hydrocarbons, carboxylic acids, esters, ethers, alcohols, waxes and lipids, and mixtures thereof.

13. A process according to claim 1 characterized by including an additive to the cellulose, cellulose derivative or any mixture thereof, before the mechanical treatment and thereafter dissolving it from the matrices in order to further increase their porosity.

14. A process tor the preparation of tablets characterized by that the porous cellulose matrices manufactured according to claim 1 are admixed, prior to compaction, with bioactive substances or granules containing bioactive substances, in order to improve the tabletting process and/or tablet properties and thereafter compressed to tablets.

15. A process according to claim 5 characterized by that the cellulose, cellulose derivative or any mixture thereof, prior to mechanical treatment, contains less than 0.15% (w/w) of ether-soluble substances according to to the test method for powdered cellulose in British Pharmacopoeia 1993.

16. A process according to claim 6 characterized by that the cellulose, cellulose derivative or any mixture thereof, prior to mechanical treatment, contains less than 1.0% (w/w) of water-soluble substances according to the test method for powdered cellulose in British Pharmacopoeia 1993.

17. A multiple unit preparation containing at least one bioactive substance comprising porous cellulose matrice particles prepared according to claim 7.

18. A multiple unit preparation according to claim 17 wherein a fraction of the matrices re-expands by swelling in contact with an aqueous fluid and thereby delivers an initial amount of bioactive substance.

19. A tablet containing at least one bioactive substance prepared by compression of the porous cellulose matrices prepared according to claim 1.

20. A tablet according to claim 19 characterized in that a fraction of the porous cellulose matrices used in the compression re-expands by swelling and thereby disintegrates the tablet.

21. A multiple unit preparation according to claim 17 characterized in that the porous cellulose matrices, prior to optional loading, contains less than 0.15% (w/w) of ether-soluble substances and less than 1.0% (w/w) of water-soluble substances according to the test method for powdered cellulose in British Pharmacopoeia 1993.

22. A tablet according to claim 19 characterized in that the porous cellulose matrices, prior to optional loading, contains less than 0.15% (w/w) of ether-soluble substances and less than 1.0% (w/w) of water-soluble substances according to the test method for powdered cellulose in British Pharmacopoeia 1993.

23. The process of claim 1 wherein said size is 0.3 to 2 mm and said tap density is less that 0.7 g/ml.

24. A process according to claim 2, wherein the spraying device is an atomizer.

25. A process according to claim 3, wherein the cellulose derivative is ethyl cellulose.

26. A process according to claim 1, wherein the solids content is at least 80%.

27. A process according to claim 26, wherein the solids content is at least 90%.

28. A process according to claim 5 wherein the release rate of the bioactive substance or substances is modified by applying a release controlling coating on the surface of said particles.

29. A process for the manufacture of porous cellulose matrices from a cellulose raw material selected from the group consisting of celluloses, carboxy methylcellulose and any mixture thereof, having a mean fiber length less than the desired mean diameter of the resulting particles and further having a solids content of at least 70%, by mechanically treating said cellulose raw material with a low-adhesion mixing device during a controlled, gradual addition of an aqueous mixing fluid, into mainly spherical particles, and finally drying the resulting particles to obtain dry porous cellulose matrices with a particle size distribution in the range of about 0.1 to 3 mm with reference to the largest diameter of the particles, and a tap bulk density less than 0.8 mg/ml in the dry state.

30. A process for the manufacture of porous cellulose matrices from a cellulose raw material selected from the group consisting of celluloses, cellulose chemical derivatives and any mixture thereof, having a mean fiber length less than the desired mean diameter of the resulting particles and further having a solids content of at least 80%, by mechanically treating said cellulose raw material with a low-adhesion mixing device during a controlled, gradual addition of an aqueous mixing fluid, into mainly spherical particles, and finally drying the resulting particles to obtain dry porous cellulose matrices with a particle size distribution in the range of about 0.1 to 3 mm with reference to the largest diameter of the particles, and a tap bulk density less than 0.8 mg/ml in the dry state.

* * * * *